(12) United States Patent
Davis et al.

(10) Patent No.: US 8,999,312 B2
(45) Date of Patent: Apr. 7, 2015

(54) USE OF PBO-PEO-PBO BLOCK COPOLYMERS IN OPHTHALMIC COMPOSITIONS

(75) Inventors: James W. Davis, Argyle, TX (US); Howard Allen Ketelson, Dallas, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 13/151,991

(22) Filed: Jun. 2, 2011

(65) Prior Publication Data

US 2011/0300019 A1 Dec. 8, 2011

Related U.S. Application Data

(60) Provisional application No. 61/350,787, filed on Jun. 2, 2010.

(51) Int. Cl.
| | |
|---|---|
| *C09K 13/00* | (2006.01) |
| *A61L 2/00* | (2006.01) |
| *C09K 3/00* | (2006.01) |
| *A61L 9/01* | (2006.01) |

(Continued)

(52) U.S. Cl.
CPC .............. *C11D 3/48* (2013.01); *A61L 12/124* (2013.01); *A61L 12/142* (2013.01); *C11D 1/008* (2013.01); *C11D 3/0078* (2013.01); *C11D 3/3947* (2013.01)

(58) Field of Classification Search
CPC ...... A61L 9/01; C11D 3/0078; A01N 1/0215; A01N 25/00
USPC .................... 424/76.8; 252/79.1, 186.1, 380; 510/108; 422/1, 28, 32
See application file for complete search history.

(56) References Cited

U.S. PATENT DOCUMENTS

| 2,174,761 | A | 10/1939 | Schuette et al. |
| 2,674,619 | A | 4/1954 | Lundsted |

(Continued)

FOREIGN PATENT DOCUMENTS

| EP | 0894849 A1 | 3/1991 |
| GB | 722746 | 1/1955 |
| WO | 03043668 | 5/2003 |

OTHER PUBLICATIONS

Nace, Contrasts in the Surface Activity of Polyoxypropylene and Polyoxybutylene-based Block Copolymer Surfactants; JAOCS, vol. 73, No. 1, (1996) pp. 1-9.

(Continued)

*Primary Examiner* — Monzer R Chorbaji
(74) *Attorney, Agent, or Firm* — Michael Rein

(57) ABSTRACT

The use of poly(oxybutylene)-poly(oxyethylene)-poly(oxybutylene) block copolymers in pharmaceutical compositions useful, for modifying the surfaces of contact lenses and other medical devices is disclosed. The present invention is based in-part on a discovery that this class of compounds is particularly efficient in wetting hydrophobic surfaces, such as the surfaces of silicone hydrogel contact lenses and other types of ophthalmic lenses, but do not induce foaming when used in conjunction with a peroxide-based contact lens disinfection regimen. Such compounds may also be useful for cleaning purposes. The use of the compounds as surfactants in peroxide-based compositions for disinfecting contact lenses therefore represents a preferred embodiment of the present invention.

18 Claims, 2 Drawing Sheets

(51) Int. Cl.

| | |
|---|---|
| *C11D 3/48* | (2006.01) |
| *A61L 12/12* | (2006.01) |
| *A61L 12/14* | (2006.01) |
| *C11D 1/00* | (2006.01) |
| *C11D 3/00* | (2006.01) |
| *C11D 3/39* | (2006.01) |

(56) References Cited

U.S. PATENT DOCUMENTS

| | | | |
|---|---|---|---|
| 2,828,345 | A | 3/1958 | Spriggs |
| 3,050,511 | A | 8/1962 | Szwarc |
| 3,829,506 | A | 8/1974 | Schmolka et al. |
| 4,057,598 | A | 11/1977 | Lundberg et al. |
| 4,104,824 | A | 8/1978 | Lundberg et al. |
| 4,130,517 | A | 12/1978 | Lundberg et al. |
| 4,360,451 | A | 11/1982 | Schmolka |
| 4,902,834 | A | 2/1990 | Otten et al. |
| 5,037,647 | A | 8/1991 | Chowhan et al. |
| 5,075,400 | A | 12/1991 | Andrade et al. |
| 5,277,911 | A | 1/1994 | Viegas et al. |
| 5,342,620 | A | 8/1994 | Chowhan |
| 5,370,744 | A | 12/1994 | Chowhan et al. |
| 5,480,633 | A | 1/1996 | Simion et al. |
| 5,505,953 | A | 4/1996 | Chowhan |
| 5,523,012 | A | 6/1996 | Winterton et al. |
| 5,631,005 | A | 5/1997 | Dassanayake et al. |
| 5,746,972 | A | 5/1998 | Park et al. |
| 5,756,443 | A | 5/1998 | Inoue et al. |
| 5,773,396 | A | 6/1998 | Zhang et al. |
| 5,811,466 | A | 9/1998 | Chowhan et al. |
| 5,981,255 | A | 11/1999 | Miyota et al. |
| 6,004,923 | A | 12/1999 | Oftring et al. |
| 6,057,283 | A | 5/2000 | Oftring et al. |
| 6,143,799 | A | 11/2000 | Chowhan et al. |
| 6,204,238 | B1 | 3/2001 | Oftring et al. |
| 6,319,464 | B1 | 11/2001 | Asgharian |
| 6,320,064 | B1 | 11/2001 | Oftring et al. |
| 6,365,636 | B1 | 4/2002 | Chowhan et al. |
| 6,503,497 | B2 | 1/2003 | Chowhan et al. |
| 6,656,504 | B1 | 12/2003 | Bosch et al. |
| 6,664,294 | B1 | 12/2003 | Park et al. |
| 6,849,253 | B2 | 2/2005 | Chowhan et al. |
| 7,022,654 | B2 | 4/2006 | Tsao |
| 7,282,178 | B2 | 10/2007 | Salamone et al. |
| 7,666,354 | B2 * | 2/2010 | Kawakami et al. ............. 422/28 |
| 2002/0064514 | A1 | 5/2002 | Viegas et al. |
| 2003/0118472 | A1 * | 6/2003 | McKee et al. .................. 422/28 |
| 2004/0052746 | A1 | 3/2004 | Tamareselvy et al. |
| 2004/0241130 | A1 | 12/2004 | Tamareselvy et al. |
| 2005/0250661 | A1 | 11/2005 | Bragulla |
| 2008/0138310 | A1 * | 6/2008 | Ketelson et al. ........... 424/78.04 |
| 2011/0151017 | A1 | 6/2011 | Ketelson et al. |

OTHER PUBLICATIONS

Yu, et al., Association of Diblock and Triblock Copolymers of Ethylene Oxide and Butylene Oxide in Aqueous Solution, Langmuir, vol. 12, (1996) pp. 3404-3412.

Yang, et al. Effect of Block Structure on the Micellization and Gelation of Aqueous Solutions of Copolymers of Ethylene Oxideand Butylene Oxide; Macromolecules; vol. 27; (1994); pp. 2371-2379.

Ketelson, et al.; Dynamic Wettability Properties of a Soft Contact Lens Hydrogel; Colloids and Surfaces B: Biointerfaces; vol. 40; (2005); pp. 1-9.

Bedells, et al.; Micellisation of Diblock Copoly(oxyethylene/oxybutylene) in Aqueous Solution; J. Chem. Soc. Faraday Trans; vol. 89; No. 8; (1993); pp. 1235-1242.

Yang, et al.; Micellization of Diblock and Triblock Copolymers in Aqueous Solution. New Results for Oxyethylene/ Oxpropylene, and Oxyethylene/Alkyl Systems; Langmuir; vol. 11; (1995); pp. 4708-4711.

Kelarakis, et al.; Temperature Dependencies of the Critical Micelle Concentrations of Diblock Oxyethylene/Oxybutylene Copolymers. A Case of Athermal Micellization; Macromolecules; vol. 31; (1998); pp. 944-946.

Chaibundit, et al.; Association Properties of Triblock Copolymers in Aqueous Solution: Copolymers of Ethylene Oxide and 1,2-Butylene Oxide with Long E-blocks; Langmuir; vol. 16; (2000); pp. 9645-9652.

Yang, et al.; Association of Triblock Copolymers of Ethylene Oxide and Butylene Oxide in Aqueous Solution. A Study of BnEmBn Copolymers, Macromolecules, 1996, pp. 670-680, vol. 29.

Liu, et al., Self-Assembly of Poly(oxybutylene)-Poly(oxyethylene)-Poly(oxybutylene) (B6E46B6) Triblock Copolymer in Aqueous Solution, J. Phys. Chem. B, 1997, pp. 8808-8815, vol. 101.

Nace; Nonionic Surfactants: Polyoxyalkylene Block Copolymers, Chapter 1, pp. 1-30, 1996.

International Search Report for PCT/US2011/038927, Publication No. WO2011/153349, dated Sep. 9, 2011, 4 pages.

PCT International Preliminary Report on Patentability and Written Opinion of the International Searching Authority, International Application No. PCT/US2011/038927, dated Dec. 4, 2012, 6 pages.

* cited by examiner

USE OF PBO-PEO-PBO BLOCK COPOLYMERS IN OPHTHALMIC COMPOSITIONS

CROSS-REFERENCE TO RELATED APPLICATIONS

This application claims priority under 35 U.S.C. §119 to U.S. Provisional Patent Application No. 61/350,787, filed Jun. 2, 2010, the entire contents of which are incorporated herein by reference.

FIELD OF THE INVENTION

The present invention is directed to ophthalmic compositions containing one or more block copolymers referred to as (polyoxybutylene)-(polyoxyethylene)-(polyoxybutylene) block copolymers ("PBO-PEO-PBO"). The invention is particularly directed to the use of PBO-PEO-PBO block copolymers as non-foaming wetting agents in peroxide-based compositions for disinfecting contact lenses.

BACKGROUND OF THE INVENTION

Disinfecting compositions are frequently used in conjunction with the use of contact lenses to keep lenses clean and free from contaminants including potentially harmful bacteria and fungi. A variety of disinfecting compositions for contact lenses are known. Hydrogen peroxide systems, in particular, 3% hydrogen peroxide, are in common use. Hydrogen peroxide is strongly biocidal and also is a strong oxidizing agent which positively impacts cleaning. However, hydrogen peroxide at the 3% level is also toxic to the eye, and therefore the high levels of hydrogen peroxide used to achieve disinfection must be decomposed to water and oxygen before the lens is safe to reinsert into the eye. This process is known as neutralization or inactivation. Typically, contact lens disinfection systems employ either an enzymic catalyst such as catalase or a metal-based catalyst such as platinum to effect neutralization. A typical disinfection process involves placing a contact lens into a hydrogen-peroxide containing disinfecting solution for a certain period of time, thereby achieving disinfection, followed by a neutralization period whereby the hydrogen peroxide is decomposed, typically by employing a catalytic agent.

Various additional agents may be added to the peroxide solutions to improve cleaning and/or disinfection. For example, surface-active agents may enhance the cleaning or disinfecting properties of the solution. However, these types of agents may also lead to excessive foaming as gas is released during neutralization.

To help ensure that the disinfection is adequate, rubbing and rinsing steps are also frequently recommended. However, these are additional steps that some consumers may not always perform consistently, and so there has been an ongoing effort to design disinfecting systems that do not require the user to perform additional steps such as rubbing or rinsing.

Contact lenses may be broadly divided into two categories, rigid gas-permeable lenses, and soft, hydrogel lenses, although hybrids and other types of lenses exist. Soft or hydrogel lenses have become popular in part because they are comfortable to wear and do not require a period of adaptation. Hydrogels are water swollen three-dimensional polymeric networks that are used in a variety of biomedical applications including drug delivery agents, prosthetic devices and contact lenses. It is well established that the surface characteristics of hydrogels are determined by the orientation of hydrophobic and hydrophilic moieties of the macromolecules. See, e.g., Ketelson et al., Colloids and Surfaces B: Biointerfaces, Vol. 40, pages 1-9 (2005).

Because contact lenses are in intimate contact with the corneal surface and the human tear film, which is composed mainly of proteins, lipids, inorganic cations (e.g., calcium) and mucin, the biocompatibility characteristics of the lenses are directly affected by the surface wettability properties of the hydrogel materials, from which the lenses are formed. In particular, evaluating the surface wettability properties of a lens material is important because such properties affect the stability of the tear film. To maintain a stable tear film, a contact lens material must have hydrophilic surface properties. If the contact lens material becomes hydrophobic, the tear film may be disrupted. To determine the wettability of a surface via an aqueous solution, such as human lacrimal fluid, i.e., tears, the contact angle is measured. The spreading of an aqueous fluid on a surface indicates that the surface is hydrophilic, thereby resulting in a low contact angle. The surface is hydrophobic if a drop of aqueous fluid does not spread, thereby resulting in a high contact angle.

A new family of contact lens materials, silicone hydrogels ("SiH"), is gradually replacing traditional hydrogels as the material of choice for extended wear soft contact lenses. Silicone hydrogel materials have significantly higher oxygen permeability than traditional soft lens hydrogels due to the presence of siloxane functional groups. Additionally, the presence of siloxane groups in SiH materials results in a lens surface having hydrophobic properties. An example of a SiH lens is the Acuvue Advance® contact lenses marketed by Johnson & Johnson.

Various techniques, for example, plasma surface treatments and incorporation of molecules within the lens material, have been utilized in order to provide a biocompatible, hydrophilic and wettable lens surface. Although modifying the surface can improve biocompatibility, it has also been reported that some silicone hydrogel materials accumulate lipids over time, and that this build-up may result in a decrease in the wettability of the silicone hydrogel lens material and surface.

The wettability characteristics of the surfaces of contact lenses may also be modified by reducing the amount of hydrophobization on the surfaces. Surfactants have been utilized in prior compositions for treating contact lenses, for example poloxamers and poloxamines, such as the Pluronic® and Tetronic® brands of surfactants, which are poly(oxyethylene)-poly(oxypropylene) ("PEO-PPO") block copolymers, have been used extensively in prior products utilized to treat contact lenses. However, such surfactants do not wet SiH lenses efficiently.

U.S. Pat. No. 5,523,012 (Winterton et al.) discloses buffered peroxide formulations with poloxamine or poloxamer surface active agents.

U.S. Pat. No. 5,746,972 (Park et al.) discloses compositions containing hydrogen peroxide and a solid ethylene oxide/propylene oxide block copolymer surfactant having at least 70% by weight polyethylene oxide.

U.S. Pat. No. 7,022,654 (Tsao) discloses compositions containing hydrogen peroxide and hydrophobe-hydrophile block copolymers where the hydrophile component constitutes less than 50 weight percent of the block copolymer.

A new class of surface-active agents has been found to efficiently wet SiH lenses, namely, EO-BO copolymers. However, it has been found that EO-BO copolymers may cause excessive foaming when used in peroxide-based disinfecting solutions during neutralization, for example, with platinum catalyst discs.

U.S. Patent Application Publication No. 2008/0138310 (Ketelson et al.) discloses the use of poly(oxyethylene)-poly(oxybutylene) block copolymers in pharmaceutical compositions.

In view of the foregoing, there is a need for new methods and compositions for improving the wettability of (SiH) contact lenses as well as older lens types while minimizing foaming of peroxide-based contact lens disinfection formulations.

SUMMARY OF THE INVENTION

The present invention is directed to the use of block copolymers referred to as (polyoxybutylene)-(polyoxyethylene)-(polyoxybutylene) block copolymers ("PBO-PEO-PBO") to modify the surface properties of ophthalmic medical devices, so as to enhance the wettability of the devices, and facilitate cleaning of the devices. The PBO-PEO-PBO block copolymers described herein may be contained in various types of compositions for treating medical devices, such as wetting solutions, soaking solutions, cleaning and comfort solutions, and disinfection solutions. The primary function of the PBO-PEO-PBO block copolymers in the compositions of the present invention is to treat the surface of a medical device, particularly an ophthalmic device, such as a contact lens or an intraocular lens. Such treatment facilitates the wettability of the device and/or the cleaning of the device. This surface treatment has been found to be particularly effective relative to enhancing the wettability of SiH contact lenses. The present invention is based on a new finding that certain PBO-PEO-PBO block copolymers can be used with peroxide-based contact lens formulations to effectively modify contact lens surface properties at low concentrations, for example, improving the wetting properties of SiH contact lenses, without causing excessive foaming during platinum-induced neutralization.

Wettability may be determined by measuring the contact angle, θ, from the Young-Dupré equation as follows:

$$\gamma_{LV}\cos\theta = \gamma_{SV} - \gamma_{SL}$$

where γ is the interfacial tension between two phases indicated by the subscripts (S: solid, L: liquid, and V: vapor). Increasing $\gamma_{SL}$ and/or $\gamma_{LV}$ increases the contact angle θ. For example, a water droplet beads up on a hydrophobic surface, displaying high contact angle at the water-solid interface (e.g. a contact lens surface soaked in saline). Water spreads out over a hydrophilic surface, displaying low contact angles (e.g. a contact lens soaked in a surfactant solution).

When a surfactant is present in a peroxide solution, foaming may occur due to the release of oxygen from the neutralization effect of the peroxide with the catalyst. The volume of foam can be substantial and when the amount of foaming is excessive the foaming may interfere with the procedures necessary to effectively disinfect a contact lens, for example, when the volume of foam exceeds the dimensions of the container used.

In one embodiment the present invention is directed to a composition comprising an effective amount of at least one poly(oxybutylene)-poly(oxyethylene)-poly(oxybutylene) block copolymer having a molecular weight in the range of 500 to 10,000 Daltons, whereby the composition, when combined with a peroxide disinfecting solution, does not cause excessive foaming upon neutralization.

In another embodiment the present invention is directed to an ophthalmic composition for disinfecting contact lenses comprising an effective amount of at least one poly(oxybutylene)-poly(oxyethylene)-poly(oxybutylene) block copolymer having a molecular weight in the range of 500 to 12,000 Daltons and a disinfecting amount of peroxide and an ophthalmically acceptable vehicle therefor.

In another embodiment the present invention is directed to a method of improving the wetting properties of a peroxide-based contact lens disinfection composition, said method comprising adding to a composition comprising peroxide and a poly(oxyethylene)-poly(oxypropylene) block copolymer an effective amount of a poly(oxybutylene)-poly(oxyethylene)-poly(oxybutylene) block copolymer.

The present invention is more fully discussed with the aid of the following figures and detailed description below.

DETAILED DESCRIPTION OF INVENTION

Figure 1:
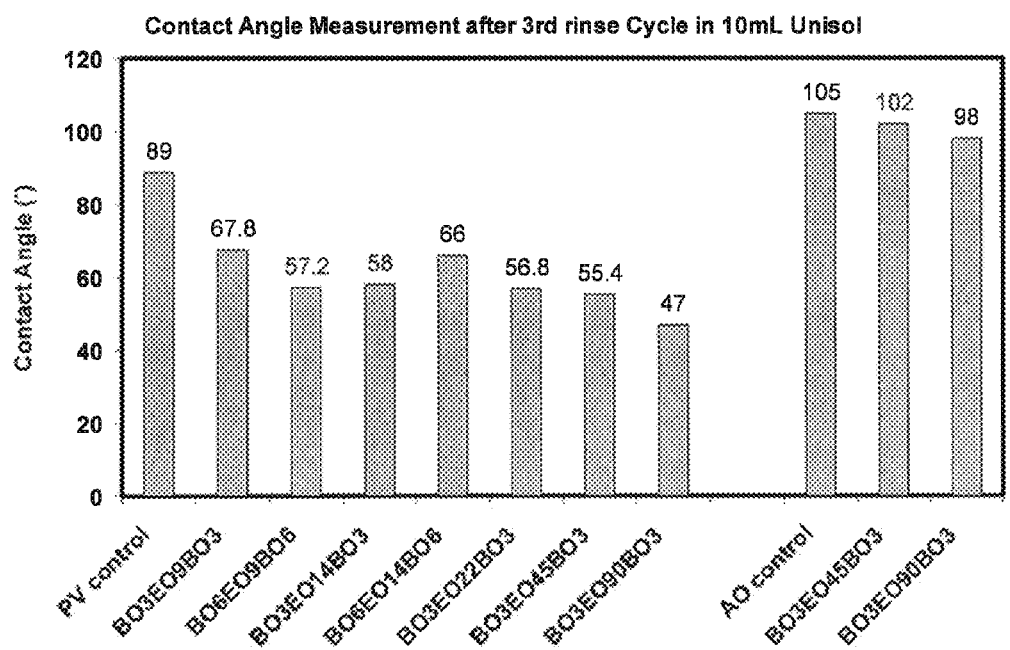
FIG. 1 is a graph of contact angle measurements for selected PBO-PEO-PBO copolymers.

As utilized herein, the following abbreviations and terms, unless otherwise indicated, shall be understood to have the following meanings:

The abbreviation "SiH" means silicone hydrogel.

The abbreviation "PEO-PPO" means poly(oxyethylene)-poly(oxypropylene).

The abbreviation "PBO-PEO-PBO" means poly(oxybutylene)-poly(oxyethylene)-poly(oxybutylene).

The abbreviation "PHMB" means polyhexamethylene biguanide.

The abbreviation "mOsm/kg" means milliosmoles/kilogram of water.

The abbreviation "pHEMA" means poly(2-hydroxyethyl methacrylate).

The abbreviation "HLB" means hydrophilic-lipophilic balance.

The abbreviation "EO" means oxyethylene.

The abbreviation "BO" means oxybutylene.

The term "contact angle" is a quantitative measure of the wetting of a solid by a liquid and defined geometrically as the angle formed by a liquid where liquid, gas and solid phases intersect. Alternative, related terms that may be used herein include "wetting angle" or "advancing contact angle."

The term "hydrophilic" means having a strong affinity for water. Alternative, related terms that may be used herein include "hydrophilicity".

The term "hydrophobic" means having little or no affinity for water. Alternative, related terms that may be used herein include, "hydrophobicity".

The term "pHEMA-MAA" means contact lenses comprised of poly(2-hydroxyethyl methacrylate-co-methacrylic acid). Exemplary pHEMA-MAA lenses include "Acuvue® 2" (Johnson & Johnson).

The term "surfactant" means a substance capable of reducing the surface tension of a liquid, e.g., water or an aqueous solution, in which the substance is dissolved.

The term "wetting" means converting a hydrophobic surface whereon a liquid (e.g., water) does not spread because the liquid has an increased surface tension to a surface that is hydrophilic whereon the liquid spreads readily because its surface tension is reduced, as determined by a contact angle experiment. Alternative, related terms that may be used herein include "wettability".

The term "uptake" refers to the amount of surfactant that is absorbed and/or adsorbed by a contact lens or other medical device. Alternative terms that may be used herein include, "uptake concentration", "surfactant uptake", "uptake results", "uptake data" and "uptake concentration of surfactants".

The term "oxyethylene" means a two carbon alkylenyl group bonded to an oxygen atom, for example —$CH_2$—$CH_2O$—.

The term "oxybutylene" means a four carbon alkenyl group bonded to an oxygen atom, for example, —[$OCH_2C(CH_2CH_3)H$]—.

The term "block copolymer" is a polymer that has at least one homopolymeric chain of one monomer and at least one additional homopolymeric chain of a second monomer. Exemplary configurations of such block copolymers include branched, star, di-block, tri-block and so on.

The term "homopolymer" means a polymer formed from a single monomer; for example, polyethylene formed by polymerization of ethylene.

The term "an amount effective to disinfect" means an amount of a disinfecting agent effective in producing the desired effect of disinfecting contact lenses by substantially reducing the number of viable microorganisms present on the lenses, preferably an amount which, either singly or in combination with one or more additional disinfecting agents, is sufficient.

The term "an amount effective to clean" means an amount of a cleaning agent that facilitates removing, and is preferably effective to remove, debris or deposit material from a contact lens contacted with the cleaning agent containing composition.

The term "an amount effective to enhance wettability" means an amount of wetting agent that reduces the contact angle of a contact lens.

The term "effective amount", when not otherwise qualified, means an amount effective to enhance the wettability of a surface such as a contact lens without causing excessive foaming, for example, during neutralization of peroxide in a peroxide-based contact lens disinfecting composition.

The term "excessive foaming" means an amount of foaming that would interfere with one or more of the steps needed to ensure effective disinfection, for example, when the volume of foam exceeds the dimensions of the container used for disinfection.

The term "ophthalmically acceptable vehicle" means a pharmaceutical composition having physical properties (e.g., pH and/or osmolality) that are physiologically compatible with ophthalmic tissues.

The block copolymers utilized in the present invention comprise compounds that contain hydrophilic and hydrophobic segments that can be altered to control the HLB (hydrophilic-lipophilic balance), molecular weight and other properties of the block copolymers using well known anionic polymerization techniques. More particularly, the block copolymers of the present invention are those that include a poly(oxyethylene) block as the hydrophilic component and two poly(oxybutylene) blocks as the hydrophobic component and are in the form of a tri-block copolymer. These copolymers may also be described in terms of the approximate or average value assigned to the respective repeating group, for example, $(BO)_3(EO)_{60}(BO)_3$, where the average value of the oxyethylene group is 60, and the average value of the oxybutylene groups is 3.

Preferred polymers of the present invention are tri-block copolymers of the following general formula:

$$(BO)_n(EO)_m(BO)_n \qquad (I)$$

wherein m is an integer having an average value of 5 to 1000 and n is an integer having an average value of 2 to 100; more preferably, m has an average value of 9 to 182 and n has an average value of 3 to 21; most preferably, m ranges from 45 to 182 and n has an average value of 2 to 4.

PBO-PEO-PBO tri-block copolymers of the following general formula are preferred:

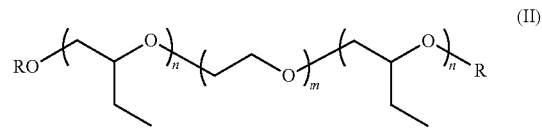

wherein R is independently selected from the group consisting of hydrogen, methyl, ethyl, propyl and butyl; m is an integer having an average value of 10 to 1000; and n is an integer having an average value of 2 to 4.

PBO-PEO-PBO tri-block copolymers of the formula (II) wherein n has an average value of 3 are particularly preferred.

Most preferred is a copolymer of formula (II) wherein one of end group R is hydrogen; m has an average value selected from the group consisting of 45, 90 and 182; and n has an average value of 3.

The PBO-PEO-PBO block copolymers utilized in the present invention have a molecular weight in the range of 500 to about 10,000 Daltons; and more preferably in the range of 800 to about 9,000 Daltons.

Maintaining a proper hydrophilic-lipophilic balance (HLB) imparts certain properties to the PBO-PEO-PBO block copolymer compositions of the present invention. For example, the HLB of the block copolymers utilized in the compositions of the present invention is directly related to the solubility, surface wettability, and interfacial surface activity properties of the compositions of the present invention.

The BO portion of the block copolymer of formula (I) is hydrophobic and is primarily responsible for the wettability properties of the compositions described herein. The EO portion of the copolymer provides the compositions with hydrophilic properties, but more importantly, it is this portion of the co-polymer that determines the aqueous solubility of the copolymers. Although it is possible to utilize solubilizing agents in the compositions of the present invention, in which case the ratio of the length EO to BO segments is somewhat less critical, it is preferred to utilize copolymers that do not require solubilizing agents, as such compounds may disrupt or modify the HLB, which in turn may adversely affect the wettability properties of the compositions, cause ocular irritation, or create other concerns.

The foregoing PBO-PEO-PBO block copolymers may be prepared by the application or adaptation of known methods described in the literature, for example, as described in Yang, Z.; Pickard, S.; Deng, N.-J.; Barlow, R. J.; Attwood, D.; Booth, C. *Macromolecules* 1994, 27, 2371-2379; Yang, Y.-W.; Yang, Z.; Zhou, Z.-K.; Attwood, D.; Booth, C. *Macromolecules* 1996, 29, 670-680; Liu, T.; Zhou, Z.; Wu C.; Chu B.; Schneider, a K.; Nace, V. M., J. Phys. Chem. B. 1997, 101, 8808-8815; and Nace, V. M., in Nonionic Surfactants: Polyoxyalkylene Block Copolymers, 1996, Chapter 1, 1-30, the entire contents of each of which are hereby incorporated in the present specification by reference. The foregoing PBO-PEO-PBO block copolymers may also be prepared by the application or adaptation of known methods described in U.S. Pat. No. 2,828,345 (Spriggs), and U.S. Pat. No. 4,902,834 (Often et al.), the entire contents of each of which are hereby incorporated into the present specification by reference.

The PBO-PEO-PBO block copolymers described above may be synthesized using a well defined polyethylene glycol (PEG) polymer by controlled addition of oxybutylene to the primary hydroxyl groups of the PEG polymer. For example, the PBO-PEO-PBO tri-block copolymer $(BO)_n(EO)_m(BO)_n$ may be prepared by sequential anionic polymerization of ethylene oxide and butylene oxide according to the following general reaction scheme:

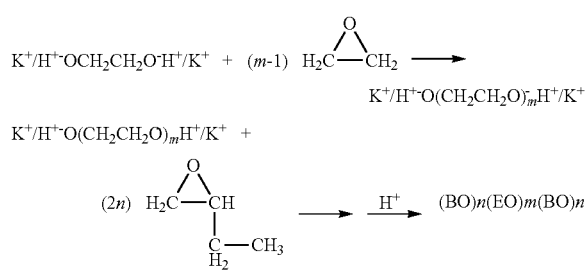

The tri-block copolymers of the present invention may be characterized according to known techniques, for example, gel permeation chromatography (GPC) and nuclear magnetic resonance spectroscopy (NMR).

The PBO-PEO-PBO block copolymers of the present invention may have free hydroxyl end groups, or, alternatively, one or both of the block end groups may be "capped", for example, with an alkyl group, preferably a methyl, ethyl, propyl or butyl group.

The PBO-PEO-PBO block copolymers of the present invention may also be functionalized with reactive end groups for specific surface reactions to covalently bind the polymer to a surface or prepare a new polymer material. The PBO-PEO-PBO block copolymers that may be utilized in the present invention are not limited relative to structure or molecular weight, so long as the block copolymers are soluble in aqueous solutions and are non-toxic to ophthalmic tissue at concentrations on the order of those described herein.

The amount of PBO-PEO-PBO block copolymer required in the compositions of the present invention may vary depending on the particular block copolymer selected and the particular purpose or function for which the block copolymer is being utilized (e.g., contact lens wetting, contact lens cleaning and/or inhibition of uptake of lipids or other biomolecules), as well as on other variables, such as the identity and physical properties of other components in the compositions. The determination of the ideal concentration of a particular copolymer in a given composition can be determined through routine testing. Such concentrations are referred to herein by means of the function to be performed by the PBO-PEO-PBO block copolymers, such as, "an amount effective to clean", "an amount effective to enhance wettability", "an amount effective to inhibit the uptake of biomolecules", and so on. When not otherwise qualified, the term "effective amount" refers to an amount effective to enhance the wettability of a contact lens without causing excessive foaming during neutralization of peroxide in a peroxide-based contact lens disinfecting composition.

The total amount of PBO-PEO-PBO block copolymers contained in the compositions of the present invention will typically be in the range of 0.001 to about 1 weight/volume percent ("w/v %"), preferably about 0.05 to 0.5 w/v %, more preferably between about 0.1 to 0.3 w/v %, most preferably about 0.2 w/v %.

The above-described block copolymers and variations thereof may be used in combination, either with each other, or with other types of polymers. For example, PBO-PEO-PBO block copolymers or variations thereof may be used in combination with nonionic surfactants (e.g., poloxamer and poloxamine block copolymers, such as the Tetronic® brand of surfactants available from BASF) to provide additive or synergistic effects where appropriate.

The compositions may also contain one or more poly(oxyethylene)-poly(oxypropylene) block copolymers such as poloxamer or poloxamine copolymers (e.g., poloxamine 1304, which is commercially available as "Tetronic® 1304"). Poloxamines, also known by the trade name Tetronic™, are tetrafunctional block copolymers which contain four polyethylene oxide (PEO)-polypropylene oxide (PPO) chains joined to the nitrogen atoms of a central ethylene diamine moiety. Poloxamers, also known by the trade name Pluronic™, are nonionic block copolymers composed of a central hydrophobic chain of poly(oxypropylene) flanked by two hydrophilic chains of poly(oxyethylene). In a preferred embodiment, the PBO-PEO-PBO block polymers of the present invention are used in combination with poloxamer block copolymers. A particularly preferred embodiment of the present invention is a composition comprising a block copolymer of the formula

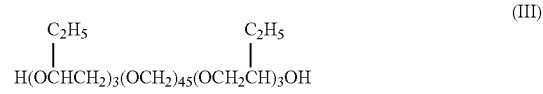

and poloxamer Pluronic 1784, a difunctional block copolymer available commercially (BASF Corporation, Mount Olive, N.J.), which may be represented by the formula

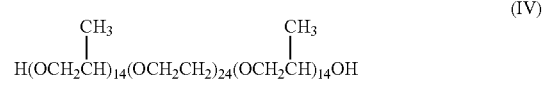

One or more of the above-described poly(oxyethylene)-poly(oxypropylene) block copolymers may be contained in the compositions of the present invention in an amount effective to facilitate wetting and/or cleaning of contact lenses, which is referred to herein as an "effective amount". Such amount will typically be in the range of 0.001 to about 1 weight/volume percent ("w/v %"), preferably about 0.01 to 0.5 w/v %.

The block copolymers of the present invention may also be combined with other components commonly utilized in products for treating contact lenses, such as rheology modifiers, enzymes, antimicrobial agents, surfactants, chelating agents, buffering agents or combinations thereof.

A variety of buffering agents may be utilized in the compositions of the present invention, such as basic acetates, phosphates, boric acid, sodium borates, sodium citrates, citric acid, nitrates, sulfates, lactates, carbonates, bicarbonates, and combinations thereof. Buffers, when present, may be used in a concentration range of 0.001% to 2%, to maintain the composition at a pH range of about 4 to about 9. Borate and polyol systems may also be used to provide buffering, to enhance antimicrobial activity, or to provide both buffering and an enhancement of antimicrobial activity, or other useful properties to the compositions of the invention. The borate and polyol systems which may be used include those described in U.S. Pat. Nos. 6,849,253; 6,503,497; 6365,636; 6,143,799; 5,811,466; 5,505,953; and 5,342,620; the entire contents of each are hereby incorporated in the present specification by reference.

Stabilizing agents may also be included in the compositions of the present invention, in order to control the rate of decomposition of peroxide. Various types of stabilizing agents may be used, however, preferred stabilizing agents are those based on diethylenetriamine penta(methylene phosphonic acid), for example, Dequest® 2060s (Thermphos USA Corp., Anniston Ala.).

The present invention may be better understood by reference to the following examples, which are provided to further illustrate certain preferred embodiments of the invention, and should in no way be construed as limiting the scope of the invention. In the following examples, various methods known to one skilled in the art may be employed to measure the contact angle for lenses according to the present invention. Exemplary methods include, but are not limited to, the Sessile method or the Captive Bubble method, as described in U.S. Patent Application Publication No. 2008/0138310 (Ketelson et al.), the entire contents of which is hereby incorporated into the present specification by reference.

Example 1

A series of PBO-PEO-PBO copolymers were investigated for foaming and wettability studies. Block lengths were confirmed by NMR. The BO units were fixed at 3 and 6 units with EO units ranging from 9 to 182. The increase in EO is to provide improved wettability, measured through Contact Angle, without sacrificing increased foaming, measured by visualization of foaming during neutralization. The Molecular Weight (Mw), confirmed by GPC, ranged from 830 g/mol up to 8442/mol.

TABLE 1

Investigation of a series of PBO-PEO-PBO copolymers for foaming and wettability.

| Component | $M_w$ | Investigated Foaming | Investigated Wettability |
|---|---|---|---|
| $BO_3EO_9BO_3$ | 830 | ✓ | ✓ |
| $BO_3EO_{14}BO_3$ | 1050 | ✓ | ✓ |
| $BO_3EO_{22}BO_3$ | 1402 | ✓ | ✓ |
| $BO_3EO_{45}BO_3$ | 2414 | ✓ | ✓ |
| $BO_3EO_{90}BO_3$ | 4394 | ✓ | ✓ |
| $BO_3EO_{136}BO_3$ | 6418 | ✓ | — |
| $BO_3EO_{182}BO_3$ | 8442 | ✓ | ✓ |
| $BO_6EO_9BO_6$ | 1262 | ✓ | — |
| $BO_6EO_{14}BO_6$ | 1482 | ✓ | — |
| $BO_6EO_{22}BO_6$ | 1834 | ✓ | — |
| $BO_6EO_{45}BO_6$ | 2846 | ✓ | — |
| $BO_6EO_{90}BO_6$ | 4824 | ✓ | — |

A step-wise experimental testing procedure was followed, whereby the PBO-PEO-PBO copolymers were first tested for excessive foaming, and then those PBO-PEO-PBO copolymers that did not cause excessive foaming were tested for wettability by investigating their contact angles. The commercially-available peroxide formula Clear Care® (CibaVision, Duluth Ga.), which contains 0.02% Pluronic 17R4, modified by the addition of 0.2% PBO-PEO-PBO, $EO_{45}BO_{11}$ and Tetronic 1304, was used to test for foaming. While the container used to evaluate foaming can vary, in the experiments described below AOSEPT Disposable Cup and Disc kits (CibaVision, Duluth Ga.), which hold approximately 20 mL of fluid, were used. To a new cup 10 mL of peroxide formulation was added. This was then capped and tightened with the platinum cartridge. The peroxide formulations where visually inspected at the beginning and intermittently (every 10 minutes) for foaming. Excessive foaming was considered to occur if solution leaked from the case. As indicated in Table 2, $BO_6EO_9BO_6$ through $_{90}BO_6$, $EO_{45}BO_{11}$ and Tetronic 1304 all foamed excessively in the modified Clear Care® formulation, while $BO_3EO_9BO_3$ through $BO_3EO_9BO_3$ did not foam excessively in the modified Clear Care® formulation. These copolymers were then used to investigate Contact Angle for silicone hydrogel lenses following a procedure described in Example 2.

TABLE 2

Results of investigation of foaming.

| Surfactant added to Clear Care | $M_w$ | Foaming upon Neutralization | Investigated Contact Angle |
|---|---|---|---|
| $BO_3EO_9BO_3$ | 830 | — | ✓ |
| $BO_3EO_{14}BO_3$ | 1050 | — | ✓ |
| $BO_3EO_{22}BO_3$ | 1402 | — | ✓ |
| $BO_3EO_{45}BO_3$ | 2414 | — | ✓ |
| $BO_3EO_{90}BO_3$ | 4394 | — | ✓ |
| $BO_6EO_9BO_6$ | 1262 | Excessive foaming | — |
| $BO_6EO_{14}BO_6$ | 1482 | Excessive foaming | — |
| $BO_6EO_{22}BO_6$ | 1834 | Excessive foaming | — |
| $BO_6EO_{45}BO_6$ | 2846 | Excessive foaming | — |
| $BO_6EO_{90}BO_6$ | 4824 | Excessive foaming | — |
| $EO_{45}BO_{11}$ | 2920 | Excessive foaming | — |
| Tetronic 1304 | 10500 | Excessive foaming | — |

Example 2

The contact angles for two silicone hydrogel lenses, AcuVue Oasys® (AO) (Johnson & Johnson Vision Care, Inc., Jacksonville Fla.) and Pure Vision® (PV) (Bausch & Lomb Inc., Rochester, N.Y.), were measured as described below. The results are reported in FIG. 1, which shows Contact Angle values after a $3^{rd}$ rinse cycle in Unisol® preservative-free saline solution (Alcon Laboratories, Inc. Fort Worth, Tex.) for Pure Vision and Acuvue Oasys contact lenses in Clear Care® formulations modified with the addition of 0.2% PBO-PEO-PBO. Clear Care® was the control for both PV and AO lenses. Contact Angle Measurements for Control Lenses: No Pre-Soaking Two brands of silicone hydrogel contact lenses (AcuVue Oasys® and Pure Vision®), were soaked in Unisol® saline solution overnight to remove residual packing solution contaminants, prior to measuring the contact angles. The lenses were then pre-soaked for 24 hours in Unisol with 0.2% PBO-PEO-PBO. The contact angle of each lens was then measured according to the Sessile drop method, as described below, at room temperature, i.e, 23° C.±0.5. Contact angle measurements for the control lenses did not include a pre-soaking step.

Sessile Drop Method

A video based contact angle measuring system (OCA 20) from Future Digital Scientific employing SCA20 software (Version 2.1.5 build16) was used. An accelerated approach was developed to evaluate the lens surface wettability over a specific time period. The lenses were subjected to sequential wetting and air exposure cycles to simulate the clinical contact lens wetting and drying conditions that occur during the normal blinking process. One "cycle" means that a lens was soaked in saline solution for 5 minutes, followed by an exposure of the lens to air for 1.5 minutes. The contact angles of a water droplet on the lens surface were measured within 10 seconds following each cycle. In all measurements, the left and right contact angles were determined and the mean of these contact angles was used. For each drop image, three independent fitting measurements were performed to provide three mean contact angles of the same drop image. The average of these three contact angles was determined and the precision was within ±3%.

The steps of a typical experimental protocol are described as follows:
1) Add 10 mL of UNISOL 4 to a 20 mL scintillation vial.
2) Take one lens from the blister pack and dab dry with lens tissue paper.
3) Place lens in 20 mL scintillation vial with UNISOL 4 and soak for 24 hours.
4) Take UNISOL 4® soaked lens and place in a new AOSEPT lens container. Add 10 mL of test solution (or Clear Care). Neutralize the solution for 24 hours.
5) Remove lens from the neutralized solution in the Aosept cartridge and place on lens mold stand.
6) After 90 seconds exposed in air, drop 54 of deionized water on lens and quickly take picture for a Contact angle measurement.
7) Place in a new 20 mL scintillation vial with 10 mL of UNISOL 4®. Allow to sit for 5 minutes.
8) Measure Contact Angle of lenses at least to 3rd rinse cycle. (Includes 90 seconds in air followed by 5 minute soak in fresh 10 mL of Unisol 4®).

PV lenses were soaked in Clear Care® modified with 0.2% PBO-PEO-PBO using the non-foaming copolymers from Table 2. Two modified Clear Care® peroxide solutions with PBO-PEO-PBO with low contact angles, $BO_3EO_{45}BO_3$ and $BO_3EO_{90}BO_3$, were investigated with AO lenses.

As can be seen from the data as shown in FIG. 1, PBO-PEO-PBO in a peroxide formulation improves the wettability of the PV and AO lenses.

Example 3

A series of formulations consisting of 3.5% Peroxide, 0.75% Sodium Borate, 0.35% Boric Acid at pH of 7.9 after neutralization were prepared with selected surfactants. The PBO-PEO-PBO surfactants were added in combination with Pluronic 17R4 to investigate their combined foaming and wettability.

TABLE 3

PBO-PEO-PBO's and Pluronic 17R4 investigated for foaming and wettability studies using borate buffered vehicle.

| Component | $M_w$ | Investigated Foaming Upon Neutralization | Investigated Contact Angle |
|---|---|---|---|
| $BO_3EO_{45}BO_3$ | 2414 | ✓ | ✓ |
| $BO_3EO_{90}BO_3$ | 4394 | ✓ | — |
| $BO_3EO_{136}BO_3$ | 6418 | ✓ | — |
| $BO_3EO_{182}BO_3$ | 8442 | ✓ | ✓ |
| Pluronic 17R4 | 2650 | ✓ | ✓ |

None of the borate buffered peroxide formulations using the PBO-PEO-PBO's in Table 3 foamed in the presence of PLURONIC 17R4 upon neutralization.

Example 4

TABLE 4

PBO-PEO-PBO and Pluronic 17R4 Borate Buffered formulations.

| Comp (% wt/% wt) | A | B | C | D | E | F | G | H | CC |
|---|---|---|---|---|---|---|---|---|---|
| Pluronic 17R4 | 0.02 | 0.02 | — | — | 0.02 | 0.02 | — | — | (0.02) |
| $BO_3EO_{45}BO_3$ | 0.02 | 0.2 | 0.02 | 0.2 | — | — | — | — | — |
| $BO_3EO_{90}BO_3$ | — | — | — | — | 0.02 | 0.2 | 0.02 | 0.2 | — |
| $Na_2B_4O_7 \times 10H_2O$ | 0.75 | 0.75 | 0.75 | 0.75 | 0.75 | 0.75 | 0.75 | 0.75 | — |
| Boric Acid | 0.35 | 0.35 | 0.35 | 0.35 | 0.35 | 0.35 | 0.35 | 0.35 | — |
| $NaH_2PO_4$ | 0.136 | 0.136 | 0.136 | 0.136 | 0.136 | 0.136 | 0.136 | 0.136 | — |
| $Na_2HPO_4$ | 0.062 | 0.062 | 0.062 | 0.062 | 0.062 | 0.062 | 0.062 | 0.062 | — |
| NaCl | 0.23 | 0.23 | 0.23 | 0.23 | 0.23 | 0.23 | 0.23 | 0.23 | — |
| DEQUEST 2060S | 0.12 | 0.12 | 0.12 | 0.12 | 0.12 | 0.12 | 0.12 | 0.12 | — |
| QS (100 mL of PW) | QS | QS | QS | QS | QS | QS | QS | QS | — |
| Hydrogen Peroxide | 3.5 | 3.5 | 3.5 | 3.5 | 3.5 | 3.5 | 3.5 | 3.5 | — |
| Foaming upon Neutralization | — | — | — | — | — | — | — | xs | — |

TABLE 5

PBO-PEO-PBO and Pluronic 17R4 Borate Buffered formulations.

| Comp (% wt/% wt) | I | J | K | L | M | N | O | P | CC |
|---|---|---|---|---|---|---|---|---|---|
| Pluronic 17R4 | 0.02 | 0.02 | — | — | 0.02 | 0.02 | — | — | (0.02) |
| $BO_3EO_{136}BO_3$ | 0.02 | 0.2 | 0.02 | 0.2 | — | — | — | — | — |
| $BO_3EO_{182}BO_3$ | — | — | — | — | 0.02 | 0.2 | 0.02 | 0.2 | — |
| $Na_2B_4O_7 \times 10H_2O$ | 0.75 | 0.75 | 0.75 | 0.75 | 0.75 | 0.75 | 0.75 | 0.75 | — |
| Boric Acid | 0.35 | 0.35 | 0.35 | 0.35 | 0.35 | 0.35 | 0.35 | 0.35 | — |
| $NaH_2PO_4$ | 0.136 | 0.136 | 0.136 | 0.136 | 0.136 | 0.136 | 0.136 | 0.136 | — |
| $Na_2HPO_4$ | 0.062 | 0.062 | 0.062 | 0.062 | 0.062 | 0.062 | 0.062 | 0.062 | — |
| NaCl | 0.23 | 0.23 | 0.23 | 0.23 | 0.23 | 0.23 | 0.23 | 0.23 | — |

TABLE 5-continued

PBO-PEO-PBO and Pluronic 17R4 Borate Buffered formulations.

| Comp (% wt/% wt) | I | J | K | L | M | N | O | P | CC |
|---|---|---|---|---|---|---|---|---|---|
| DEQUEST 2060S | 0.12 | 0.12 | 0.12 | 0.12 | 0.12 | 0.12 | 0.12 | 0.12 | — |
| QS (100 mL of PW) | QS | QS | QS | QS | QS | QS | QS | QS | — |
| Hydrogen Peroxide | 3.5 | 3.5 | 3.5 | 3.5 | 3.5 | 3.5 | 3.5 | 3.5 | — |
| Foaming upon Neutralization | — | — | xs | xs | — | — | xs | xs | — |

From Tables 4 and 5, the borate buffered peroxide formulations A-D, M, N and O were used to investigate contact angle on two types of lenses, Pure Vision (PV) and Acuvue Oasys (AO). These formulations did not foam and were at the low and high end of the EO block lengths, 45 and 182 EO units respectively. PV and AO historically have high Contact Angles, 80°-110°, reflecting low wettability of lens.

TABLE 6

PBO-PEO-PBO and Pluronic 17R4 Borate Buffered formulations used for Contact Angle Measurements for PV and AO lenses.

| Comp (% wt/% wt) | A | B | C | D | M | N | O | CC |
|---|---|---|---|---|---|---|---|---|
| Pluronic 17R4 | 0.02 | 0.02 | — | — | 0.02 | 0.02 | — | (0.02) |
| BO$_3$EO$_{45}$BO$_3$ | 0.02 | 0.2 | 0.02 | 0.2 | — | — | — | — |
| BO$_3$EO$_{182}$BO$_3$ | — | — | — | — | 0.02 | 0.2 | 0.02 | — |
| Na$_2$B$_4$O$_7$ × 10H$_2$O | 0.75 | 0.75 | 0.75 | 0.75 | 0.75 | 0.75 | 0.75 | — |
| Boric Acid | 0.35 | 0.35 | 0.35 | 0.35 | 0.35 | 0.35 | 0.35 | — |
| NaH$_2$PO$_4$ | 0.136 | 0.136 | 0.136 | 0.136 | 0.136 | 0.136 | 0.136 | — |
| Na$_2$HPO$_4$ | 0.062 | 0.062 | 0.062 | 0.062 | 0.062 | 0.062 | 0.062 | — |
| NaCl | 0.23 | 0.23 | 0.23 | 0.23 | 0.23 | 0.23 | 0.23 | — |
| DEQUEST 2060S | 0.12 | 0.12 | 0.12 | 0.12 | 0.12 | 0.12 | 0.12 | — |
| QS (100 mL of PW) | QS | QS | QS | QS | QS | QS | QS | — |
| Hydrogen Peroxide | 3.5 | 3.5 | 3.5 | 3.5 | 3.5 | 3.5 | 3.5 | — |

Figure 2:
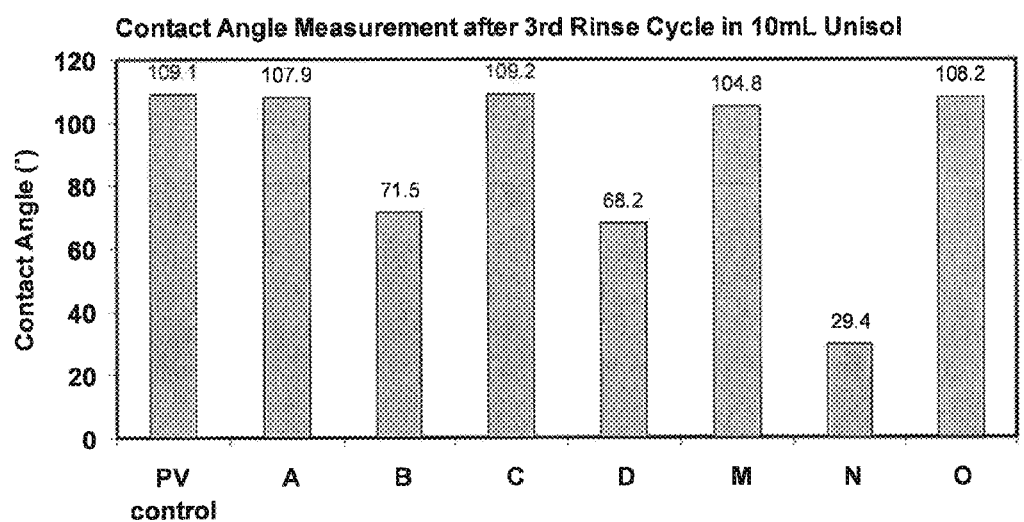
FIG. 2 is a graph of contact angle measurements for compositions containing varying amounts of $BO_3EO_{45}BO_3$, $BO_3EO_{182}BO_3$, and Pluronic 17R4.

FIG. 2 shows the results of contact angles measured after the 3rd rinse cycle in UNISOL for Pure Vision lenses in Borate Buffered formulations with PBO-PEO-PBO and with and without Pluronic 17R4. Clear Care® was the control for the PV lenses.
Formulations B and N showed better wetting trend, with lower contact angles, than the control of Clear Care® for PV lens materials. Formulation B has 0.02% PLURONIC 17R4 and 0.2% BO$_3$EO$_{45}$BO$_3$, while formulation N has 0.02% PLURONIC 17R4 and 0.2% BO$_3$EO$_{182}$BO$_3$.

We claim:

1. An ophthalmic composition for disinfecting contact lenses comprising an effective amount of at least one poly (oxybutylene)-poly(oxyethylene)-poly(oxybutylene) block copolymer of the formula (BO)n(EO)m(BO)n, wherein m is an integer having an average value of 5 to 1000 and n is an integer having an average value of 2 to 4 having a molecular weight in the range of 500 to 12,000 Daltons and a concentration of peroxide of about 3% or more and an ophthalmically acceptable vehicle therefor, wherein the composition does not foam excessively upon neutralization with a metal catalyst.

2. A composition according to claim 1, wherein m ranges from 45 to 182.

3. A composition according to claim 2, wherein the average value of m is selected from the group consisting of 45, 90 and 182 and the average value of n is 3.

4. A method of disinfecting a contact lens, said method comprising (a) contacting a contact lens with a composition according to claim 3 and (b) neutralizing said hydrogen peroxide by catalytic decomposition with a metal catalyst.

5. A method of disinfecting a contact lens, said method comprising (a) contacting a contact lens with a composition according to claim 2 and (b) neutralizing said hydrogen peroxide by catalytic decomposition with a metal catalyst.

6. A composition according claim 1, wherein the poly (oxybutylene)-poly(oxyethylene)-poly(oxybutylene) block copolymer is of the formula

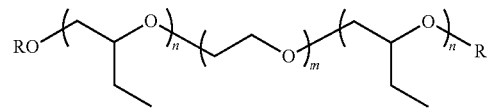

wherein R is independently selected from the group consisting of hydrogen, methyl, ethyl, propyl and butyl; m is an integer having an average value of –10 to 1000; and n is an integer having an average value of 2 to 4.

7. A composition according to claim 6, wherein R is independently selected from the group consisting of methyl and hydrogen, and the average value of m is selected from the group consisting of 45, 90 and 182, and the average value of n is 3.

8. A method of disinfecting a contact lens, said method comprising (a) contacting a contact lens with a composition according to claim 7 and (b) neutralizing said hydrogen peroxide by catalytic decomposition with a metal catalyst.

9. A method of disinfecting a contact lens, said method comprising (a) contacting a contact lens with a composition according to claim 6 and (b) neutralizing said hydrogen peroxide by catalytic decomposition with a metal catalyst.

10. A composition according to claim 1, further comprising an effective amount of a poly(oxyethylene)-poly(oxypropylene) block copolymer.

11. A composition according to claim 10, wherein the poly(oxyethylene)-poly(oxypropylene) block copolymer is of the formula.

12. A method of disinfecting a contact lens, said method comprising (a) contacting a contact lens with a composition according to claim 11 and (b) neutralizing said hydrogen peroxide by catalytic decomposition with a metal catalyst.

13. A method of disinfecting a contact lens, said method comprising (a) contacting a contact lens with a composition according to claim 10 and (b) neutralizing said hydrogen peroxide by catalytic decomposition with a metal catalyst.

14. A composition according to claim 1, wherein the solution contains said block copolymer at a concentration of 0.001 to 1% w/v.

15. A method of disinfecting a contact lens, said method comprising (a) contacting a contact lens with a composition according to claim 14 and (b) neutralizing said hydrogen peroxide by catalytic decomposition with a metal catalyst.

16. A composition according to claim 1, wherein the ratio of m to n is in the range of 14:1 to 60:1.

17. A method of disinfecting a contact lens, said method comprising (a) contacting a contact lens with a composition according to claim 16 and (b) neutralizing said hydrogen peroxide by catalytic decomposition with a metal catalyst.

18. A method of disinfecting a contact lens, said method comprising (a) contacting a contact lens with a composition according to claim 1 and (b) neutralizing said hydrogen peroxide by catalytic decomposition with a metal catalyst.

* * * * *